US006761898B1

(12) United States Patent
Cavazza

(10) Patent No.: US 6,761,898 B1
(45) Date of Patent: Jul. 13, 2004

(54) COMBINATION COMPOSITION IN THE FORM OF NUTRITIONAL SUPPLEMENT OR PHARMACEUTICAL COMPOSITION FOR THE PREVENTION AND THERAPEUTICAL TREATMENT OF DEGENERATIVE OR INFLAMMATORY ARTICULAR DISORDERS

(75) Inventor: Claudio Cavazza, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/268,723

(22) Filed: Mar. 17, 1999

(30) Foreign Application Priority Data

Mar. 19, 1998 (EP) ........................................... 98830156

(51) Int. Cl.[7] ............................ A61K 9/16; A61K 9/20; A61K 9/48; A61K 9/08; A61K 47/18; A61K 31/726; A61K 31/727

(52) U.S. Cl. ....................... 424/439; 424/451; 424/464; 424/499; 514/551; 514/54

(58) Field of Search ................................ 424/439, 488, 424/451, 464, 493, 499; 514/54, 551, 561

(56) References Cited

U.S. PATENT DOCUMENTS

| | | | |
|---|---|---|---|
| 5,037,851 A | | 8/1991 | Cavazza |
| 5,043,355 A | | 8/1991 | Cavazza |
| 5,145,871 A | | 9/1992 | Cavazza |
| 5,173,508 A | | 12/1992 | Cavazza |
| 5,192,805 A | | 3/1993 | Cavazza |
| 5,227,518 A | | 7/1993 | Cavazza |
| 5,270,472 A | | 12/1993 | Taglialatela et al. |
| 5,418,253 A | | 5/1995 | Cavazza et al. |
| 5,430,065 A | | 7/1995 | Cavazza |
| 5,432,199 A | | 7/1995 | Cavazza |
| 5,494,924 A | | 2/1996 | Cavazza et al. |
| 5,534,549 A | | 7/1996 | Tinti et al. |
| 5,543,556 A | | 8/1996 | Tinti et al. |
| 5,547,986 A | | 8/1996 | Tinti et al. |
| 5,591,450 A | | 1/1997 | Cavazza et al. |
| 5,614,556 A | | 3/1997 | Cavazza et al. |
| 5,627,212 A | | 5/1997 | Cavazza et al. |
| 5,637,305 A | | 6/1997 | Cavazza et al. |
| 5,639,767 A | | 6/1997 | Cavazza et al. |
| 5,747,536 A | | 5/1998 | Cavazza |
| 5,753,703 A | | 5/1998 | Cavazza et al. |
| 5,861,434 A | | 1/1999 | Cavazza |
| 5,863,940 A | | 1/1999 | Cavazza |
| 5,869,528 A | | 2/1999 | Cavazza |
| 5,883,127 A | | 3/1999 | Cavazza |
| 5,993,846 A | * | 11/1999 | Friedman et al. |

* cited by examiner

*Primary Examiner*—Edward J. Webman
(74) *Attorney, Agent, or Firm*—Oblon, Spivak, McClelland, Maier & Neustadt, P.C.

(57) ABSTRACT

The present invention relates to a composition, which contains L-carnitine or alkanoyl-L-carnitine, and a glucosaminoglycan or a constituent thereof, suitable for the prevention of articular disorders and for the therapeutic treatment of articular diseases.

14 Claims, No Drawings

COMBINATION COMPOSITION IN THE FORM OF NUTRITIONAL SUPPLEMENT OR PHARMACEUTICAL COMPOSITION FOR THE PREVENTION AND THERAPEUTICAL TREATMENT OF DEGENERATIVE OR INFLAMMATORY ARTICULAR DISORDERS

The present invention relates to a composition suitable both for the prevention of articular disorders and for the therapeutic treatment of articular diseases. Accordingly, the composition may take the form and exert the activity of a food or dietary supplement or of an actual medicament in the strict sense, depending upon the particular individuals in whom it is to be used and for reasons which will appear evident here below.

The most widespread articular disease is osteoarthrosis, a disease mainly affecting the hyaline cartilage and the subchondral bone with hypertrophy of the articular and periarticular tissues in the sites affected.

Osteoarthrosis sets in asymptomatically between the ages of twenty and thirty years, affecting both sexes with the same frequency, though the onset tends to be earlier in males. Around the age of forty, almost all subjects begin to present some pathological abnormality of the joints under conditions of mechanical stress, though only a relatively small number of such individuals present clear-cut symptoms.

The disease becomes universally widespread and manifest in the course of the sixth decade of life.

Osteoarthrosis is the pathological result of a complex system of mechanical, biological, biochemical and enzymatic reactions: practically every process of an infectious, metabolic, endocrine, neurological or traumatic nature capable of impairing the structure and function of the hyaline cartilage and surrounding tissues constitutes an aetiological factor for the disease.

Since the onset is asymptomatic, deceptive and gradual, treatment is generally resorted to only after onset of a clearly defined, persistent symptomatological picture, if not, indeed, in the presence of various degrees of disability and functional impairment mainly affecting the knees and hips.

The drugs of choice are aspirin and non-steroidal anti-inflammatory drugs (NSAIDs) whose adverse side effects and gastric damaging capability are well known.

It is precisely these adverse effects that induce physicians to delay the use of these therapeutic agents until such time as the symptomatological picture is stably consolidated and the resulting functional limitations threaten to impair the work, social and relational activities of the individuals affected.

There is therefore a perceived need for a preventive/therapeutic agent which, as a result of its substantial lack of toxicity and side effects, can be safely used at the first manifestation of symptoms or even earlier, once the patient has reached the age when, on average, such symptoms tend to manifest themselves. The aims of such treatment are both to delay the onset of the symptomatological picture and to combat development of the disease therapeutically.

These dual objectives—preventive and strictly therapeutic—are achieved by the composition to the present invention, which, as will be described in detail here below, consists of a new combination containing as its basic ingredients L-carnitine or a C2–C6 lower alkanoyl-L-carnitine and a glucosaminoglycan and/or glucosamino-glycan component.

This composition is characterised by an unexpected and surprising anti-inflammatory and cartilage-protecting activity. As a result of these properties the new composition can be usefully applied in the prevention and therapeutic treatment of inflammatory or degenerative articular disorders mainly related to a metabolic dysfunction of the articular tissues, whether of endogenous or exogenous origin, induced by traumas or drugs. The new composition can also be usefully employed in both the human and veterinary fields.

The use of carnitine for the prevention and cure of metabolic dysfunctions is well known. Carnitine and its alkanoyl derivatives have been shown to be useful in the treatment of myocardial ischaemia, angina pectoris, peripheral vascular disease and in the various forms of atherosclerosis.

These therapeutic activities of carnitine and its alkanoyl derivatives are related to the complex biochemical activity which these compounds are capable of exerting at cell and tissue level.

In addition to being essential for the beta-oxidation of fatty acids, carnitine plays an important antioxidant role, as demonstrated by its protective effect against hyperoxidation of the cell phospholipid membranes and against oxidative stress induced at myocardial or endothelial cell level. In particular, carnitine has been shown to be capable of intervening in carbohydrate metabolism and insulin secretion.

The metabolic role of carnitine and its alkanoyl derivatives appears, however, to be very extensive and has yet to be clarified in many of its aspects. Carnitine has been found to increase the formation of arachidonic acid from linoleic acid and, by this pathway, to play an important role in modulating inflammation.

In addition, carnitine inhibits the release of inflammatory eicosanoids by peritoneal macrophages. In particular, propionyl-L-carnitine has been shown to be capable of potentiating the effects of a cytoprotective prostaglandin such as prostacyclin.

There is no evidence of a direct effect of L-carnitine on chondrocytes and on the articular cartilage, nor on glucosamine metabolism.

There is extensive evidence, however, in the literature for the protective effect induced by proteoglycans.

As is known, proteoglycans are macromolecules produced by the chondrocytes which make up the articular cartilage. The mechanical properties of the cartilage and the functionality of the joint depend mainly on them.

Proteoglycans are formed from a central protein to which the glucosaminoglycan chains are bound. In the articular cartilages, glucosaminoglycans are represented mainly by chondroitin sulphate which is a disaccharide polymer formed from glucuronic acid and N-acetylgalactosamine sulphate.

According to whether the esterification with sulphuric acid is in position 4 or position 6 of the galactosamine, we have chondroitin-4-sulphate, which is present above all at birth and in children, or chondroitin-6-sulphate which is peculiar to adults.

With ageing, proteoglycan metabolism slows down and the levels of chondroitin sulphate diminish.

The same situation is encountered in arthrosis where an incomplete and defective biosynthesis of proteoglycans is detected. The proteoglycan aggregates in the molecular structure of the arthrotic articular cartilage are partly depolymerised and the collagen fibre is defiberized.

Glucosamines are indispensable for the biosynthesis of proteoglycans and also permit synthesis of galactosamine amino sugar necessary for the biosynthesis of glucosaminoglycans. As regards the action of glucosamines, it has been demonstrated that these are capable of stimulating repair of damaged cartilaginous tissue.

Glucosamine added to cultures of synovial fibroblasts also stimulates the incorporation of serine in chondroitin sulphate and in dermatan sulphate, preventing cortisone-induced chondrocyte damage in the rat and experimental arthrosis in the rabbit.

It is also known that the exogenous administration of glucosamine, even by the oral route, can improve arthrotic articular damage.

Whereas, on the one hand, glucosamines exert an important metabolic action at the level of the articular tissue degraded by arthrosis, glucosaminoglycans, such as chondroitin sulphate, are responsible for the mechanical and elastic properties of the articular cartilage owing to their ability to retain the water necessary for the elastic state of the cartilage itself.

It has been demonstrated that, in arthrotic situations, there is a loss of water on the part of the cartilage, which therefore becomes less elastic as a result of the reduction in chondroitin sulphate, probably due to the action of proteolytic enzymes by the chondrocytes.

The exogenous administration of chondroitin sulphate makes it possible to block these enzymes, such as elastase, which degrade the articular cartilage. In addition, the exogenous administration of chondroitin sulphate also exerts a stimulating action on proteoglycan biosynthesis. Clinical improvements in the therapy of arthrosis obtained with the use of chondroitin sulphate have been reported by numerous authors, and this therapy has been successfully combined with traditional therapy using non-steroidal anti-inflammatory drugs (NSAIDs), without, however, being advocated as an alternative to NSAIDs.

On the basis of the characteristics of the products described above, the possibility of an interaction between them was assessed by means of a series of tests performed on combinations of L-carnitine or its alkanoyl derivatives and glucosaminoglycans and/or their components. On the basis of the tests performed with these new combinations an unexpected and surprising protective effect was observed in different models of experimental inflammation, as a result of a synergic action between the components of the combinations which was thoroughly unpredictable on the basis of our existing pharmacological knowledge of L-carnitine and its alkanoyl derivatives or of the glucosaminoglycans and their components.

The composition of the present invention comprises a combination of the following components:

(a) L-carnitine or an alkanoyl-L-carnitine wherein the alkanoyl group is a straight or branched group, having 2–8, preferably 2–6, carbon atoms, or a pharmacologically acceptable salt thereof;

(b) a glucosaminoglycan and/or a constituent of glucosaminoglycan; and (c) a pharmacologically acceptable excipient.

The weight-to-weight ratio of component (a) to component (b ) ranges from 1.1 to 1:100, and preferably from 1:1 to 1:10.

The glucosaminoglycan is selected from the group comprising a chondroitin sulphate, hyaluronic acid, dermatan sulphate, keratan sulphate and heparan sulphate. Preferably, the chondroitin sulphate is either chondroitin-4-sulphate or chondroitin-6-sulphate.

The glucosaminoglycan constituent is selected from the group comprising glucosamine, glucosamine sulphate, N-acetylglucosamine, galactosamine and N-acetylgalactosamine.

The glucosaminoglycan and the glucosaminoglycan constituent can be obtained from natural products such as cartilages and collagen.

The alkanoyl-L-carnitine is preferably selected from the group comprising acetyl-L-carnitine, propionyl-L-carnitine, butyryl-L-carnitine, valeryl-L-carnitine and isovaleryl-L-carnitine. Acetyl-L-carnitine and propionyl-L-carnitine are particularly preferred.

What is meant by pharmacologically acceptable salt of L-carnitine or alkanoyl-L-carnitine is any salt of these with an acid which does not give rise to unwanted toxic or side effects. These acids are well known to pharmacologists and experts in pharmacy.

Examples of such salts, though not exclusively these, are: chloride; bromide; iodide; aspartate, acid aspartate; citrate, acid citrate; tartrate; phosphate, acid phosphate; fumarate, acid fumarate; glycerophosphate; glucose phosphate; lactate; maleate; acid maleate; orotate; oxalate, acid oxalate; sulphate, acid sulphate; trichloroacetate; trifluoroacetate and methane sulphonate.

A list of FDA-approved pharmacologically acceptable salts is published in Int. J. Pharm. 33, (1986), 201–217, and this publication is incorporated herein by reference.

The composition of the present invention may further comprise vitamins, co-enzymes, mineral substances and antioxidants.

Here below, for the sake of simplicity of presentation, reference will be made only to the combination of L-carnitine, chondroitin sulphate and glucosamine, it being understood, however, that the combinations with the above-mentioned alkanoyl-L-carnitines and the other glucosaminoglycans and/or glucosaminoglycan constituents are equally efficacious and capable of fully accomplishing the aims of the present invention.

Toxicology and Tolerability Tests

The low toxicity and good tolerability of L-carnitine and the above-mentioned alkanoyl-L-carnitines are well known, as are those of glucosamine and chondroitin sulphate.

When administered orally to both the rat and mouse, even at high doses of these compounds in combination (250 mg/kg of L-carnitine and 200 mg of chondroitin sulphate), no toxic reactions or intolerance were detectable. The same result was achieved with the parenteral administration of 150 mg/kg of L-carnitine and 100 mg/kg of chondroitin sulphate. No mortality or signs of intolerance were observed in rats treated every day for thirty consecutive days with 100 mg/kg of L-carnitine and 100 mg/kg of chondroitin sulphate.

Blood chemistry tests and histological examinations performed on these animals at the end of treatment revealed no particular damaging reactions as compared to a similar group of control animals.

Type II Collagen Arthritis Tests

Type II collagen arthritis was induced in mice according to the technique described by Trentham (Trentham D. R., Townes A. S., Kang A. H., J. Exp. Med., 146, 857, 1977).

One group of mice was immunised by means of intradermal injections of natural collagen emulsified in complete Freund's adjuvant (Difco Labs., Detroit, U.S.A.) at the base of the tail. Three weeks later these animals were re-injected intraperitoneally with the same dose of emulsified collagen. L-carnitine (50 mg/kg and 100 mg/kg), glucosamine (100 mg/kg and 200 mg/kg) and chondroitin sulphate (50 mg/kg and 100 mg/kg) were injected alone or in combination from day one after the collagen injection up to the end of the sixth week. One group of animals (control) received no treatment. The assessment of the severity of the oedema was done according to its intensity with scores ranging from 1 to 4. The results of the tests demonstrated that, whereas neither L-carnitine, glucosamine nor chondroitin sulphate when administered alone had any inhibitory effect on the development of the typical signs of arthritis, their use in combination proved highly efficacious. When L-carnitine was combined with either glucosamine or with chondroitin sulphate an approximately 50% reduction of arthrosis was obtained.

On combining L-carnitine with both glucosamine and chondroitin sulphate, the reduction in signs of arthrosis reached almost 90–100%, with no sign of arthrosis manifesting itself in the majority of animals treated.

Adjuvant-induced Arthritis Tests

Adjuvant arthritis was induced in the rat by intradermal injection of 0.6 ng of killed *Mycobacterium tubercolosis* (Difco Labs., Detroit, USA) and emulsified in liquid paraffin. The injection was performed on the sole of the animal's right paw (Walz D. T., Martino D., Mischer A., J. Pharmacol. Exp. Ther., 178, 223, 1971).

L-carnitine, glucosamine and chondroitin sulphate were injected alone or in combination, both prophylactically (100 mg/kg per compound) for 15 days after adjuvant injection and again for 15 days after adjuvant injection (200 mg/kg per compound) to observe the curative effect.

Assessment of arthrotic damage was done on the basis of a conventional rating scale and body weight.

In these tests, too, whereas the compounds when administered alone showed neither a preventive nor a curative effect on the development of arthrosis, when they were administered in combination, a curative effect was observed with an approximately 50% reduction in signs of arthrosis. Of particular interest was the fact that preventive administration of the drugs almost completely blocked the onset of arthrotic symptoms.

As with the previous results, the results of these tests reveal an unexpected preventive, protective and curative effect of the composition of the present invention, whereas the individual components of the composition were thoroughly ineffective when administered alone.

Carragenin Oedema Tests

Carragenin oedema was induced in the rat by injection of 0.1 ml of a 1% carragenin solution (Sigma Chemical) in the subplantar region of the rat's right paw. The volume of the paw was measured by means of a mercury plethysmograph one hour later and over the 5-hour period following carragenin injection.

L-carnitine, glucosamine and chondroitin sulphate were administered one hour prior to carragenin injection, both alone and in combination at doses of 50, 100 and 200 mg/kg of these compounds. In these tests, too, though to a less marked extent, whereas L-carnitine, gluocsamine and chondroitin sulphate alone failed to modify the severity of the carregenin-induced oedema, their use in combination brought about a significant reduction in oedema, close to 50% (see Table 1), especially during the first few hours of observation.

The results obtained in the tests described above are surprising and unexpected, inasmuch as the administration of the single compounds alone and not in combination produced no inhibitory effect on the experimentally induced arthrotic and inflammatory forms. The inhibitory effect appears to be marked, however, when the components are administered in combination. The greatest effect is that obtained by the simultaneous administration of L-carnitine, glucosamine and chondroitin sulphate.

A significant result is also observable with the combination of L-carnitine and glucosamine and with that of L-carnitine and chondroitin sulphate.

The unexpected pharmacological effect observed with the combination of L-carnitine, glucosamine and chondroitin sulphate enables this combination to be used effectively in the treatment of those forms of osteoarthrosis related to mechanical stress and those related to inflammatory phenomena or due to ageing.

The efficacy, good tolerability and low toxicity of this combination make the use of this treatment preferable to that of NSAIDs which present a high risk of adverse side effects and toxic reactions, especially in prolonged treatments.

TABLE 1

Effects of carnitine, glucosamine and chondroitin sulphate alone or in combination on carragenin-induced oedema in the rat.

| Substance | Dose mg/kg | % Reduction of oedema at various hours after carragenin injection 1 | 2 | 3 | 4 |
|---|---|---|---|---|---|
| L-carnitine | 100 | — | — | — | — |
| L-carnitine | 200 | — | 10 ± 0.2 | 5 ± 0.3 | — |
| Glucosamine | 100 | — | 5 ± 0.3 | 5 ± 0.5 | 5 ± 0.6 |
| Glucosamine | 200 | 5 ± 0.2 | 10 ± 0.9 | 10 ± 1.1 | 5 ± 0.5 |
| Chondroitin sulphate | 100 | 10 ± 0.3 | 10 ± 0.8 | 5 ± 0.4 | 5 ± 0.1 |
| Chondroitin sulphate | 200 | 10 ± 1.9 | 15 ± 1.1 | 20 ± 1.8 | 10 ± 1.2 |
| L-carnitine +Glucosamine +Chondroitin sulphate | 100 100 100 | 25 ± 1.9 | 30 ± 2.1 | 30 ± 2.7 | 25 ± 2.4 |
| L-carnitine +Glucosamine +Chondroitin sulphate | 200 200 200 | 20 ± 2.1 | 35 ± 2.9 | 46 ± 3.5 | 40 ± 3.1 |

By way of non-limiting examples, a number of formulations covered by the present invention are given:

| | | |
|---|---|---|
| 1) | L-carnitine | 200 mg |
| | Chondroitin-4-sulphate | 200 mg |
| 2) | L-carnitine | 200 mg |
| | Chondroitin 4-sulphate | 100 mg |
| | Chondroitin-6-sulphate | 50 mg |
| 3) | L-carnitine | 200 mg |
| | Glucosamine sulphate | 200 mg |
| 4) | L-carnitine | 200 mg |
| | Chondroitin-4-sulphate | 100 mg |
| | Glucosamine sulphate | 100 mg |
| 5) | L-carnitine | 200 mg |
| | Collagen extract (lysate) | 300 mg |
| 6) | Propionyl-L-carnitine | 250 mg |
| | Chondoitin-4-sulphate | 300 mg |
| 7) | Propionyl-L-carnitine | 250 mg |
| | Chondroitin-6-sulphate | 400 mg |
| 8) | Propionyl-L-carnitine | 250 mg |
| | Chondroitin-6-sulphate | 300 mg |
| | Glucosamine sulphate | 100 mg |
| 9) | Propionyl-L-carnitine | 250 mg |
| | Collagen extract (lysate) | 400 mg |
| 10) | Propionyl-L-carnitine | 200 mg |
| | Chondroitin-6-sulphate | 200 mg |

-continued

| | |
|---|---|
| Glucosamine sulphate | 100 mg |
| Ubidecarenone | 10 mg |
| Vitamin E | 5 mg |
| Calcium ascorbate | 50 mg |
| Selenium | 2 mg |
| Manganese | 6 mg |

The compositions of the present invention can be formulated in the form of enterally, parenterally, intramuscularly, intra-articularly or topically administrable compositions as, e.g. tablets, capsules, granulates, syrups, ointments and phials.

The suitable excipients to be used for preparing the compositions depending on the specific administration route shall be apparent to any average-skilled expert in pharmacy and pharmaceutical technology.

Glucosaminoglycan or the constituent thereof can be extracted from natural products such as cartilages and collagen.

What is claimed is:

1. A composition, consisting essentially of:

a) L-carnitine or an alkanoyl-L-carnitine, wherein the alkanoyl is a straight or branched chain having 2–8 carbon atoms, or a pharmacologically acceptable salt thereof;

b) a glucosaminoglycan; and c) a pharmacologically acceptable excipient.

2. The composition of claim 1, wherein the weight ratio of (a):(b) is from 1:1 to 1:100.

3. The composition of claim 1, wherein the glucosaminoglycan is selected from the group consisting of chondroitin sulphate, jaluronic acid, dermatan sulphate, keratan sulphate and heparan sulphate.

4. The composition of claim 3, wherein the chondroitin sulphate is selected from the group consisting of chondroitin-4-sulphate and chondroitin-6-sulphate.

5. The composition of claim 1, wherein component (a) is an alkanoyl-L-camitine which is selected from the group consisting of acetyl-L-carnitine, propionyl-L-carnitine, butyryl-L-carnitine, valeryl-L-carnitine and isovaleryl-L-carnitine.

6. The composition of claim 1, wherein the pharmacologically acceptable salt of L-carnitine or alkanoyl-L-carnitine is selected from the group consisting of chloride, bromide, iodide, aspartate, acid aspartate, citrate, acid citrate, tartrate, phosphate, acid phosphate, fumarate, acid fumarate, glycerophosphate, glucose phosphate, lactate, maleate, acid maleate, orotate, oxalate, acid oxalate, sulfate, acid sulfate, trichloroacetate, trifluoroacetate and methanesulfonate.

7. The compositon of claim 1, wherein a) is L-carnitine, and b) is chondroitin sulphate.

8. The composition of claim 1, which further consists of vitamins, co-enzymes, mineral substances or antioxidants or a combination thereof.

9. A dietary supplement, consisting essentially of an admixture of:

a) L-carnitine or an alkanoyl-L-carnitine, wherein the alkanoyl is a straight or branched chain having 2–8 carbon atoms, or a pharmacologically acceptable salt thereof; and (b) a glucosaminoglycan.

10. The dietary supplement of claim 1, wherein the glucosaminoglycan is selected from the group consisting of chondroitin sulphate, jaluronic acid, dermatan sulphate, keratan sulphate and heparan sulphate.

11. The dietary supplement of claim 10, wherein the chondrotin sulphate is selected from the group consisting of chondroitin-4-sulphate and chondroitin-6-sulphate.

12. The dietary supplement of claim 9, wherein component (a) is an akkanoyl-L-carnitine which is selected from the group consisting of acetyl-L-camitine, propionyl-L-carnitine, butyryl-L-carnitine, valeryl-L-carnitine and isovaleryl-camitine.

13. The composition of claim 1, which is in a form of an enterally, parenterally, intramuscularly, intra-articularly or topically administrable composition.

14. The composition of claim 1, which is in a form of tablets, capsules, granulates, syrups, ointments or phials.

* * * * *